United States Patent
Topper et al.

(10) Patent No.: US 7,381,212 B2
(45) Date of Patent: Jun. 3, 2008

(54) SUTURING APPARATUS AND METHOD

(75) Inventors: Brad Topper, Santa Clarita, CA (US);
Brett Bannerman, Canyon Country, CA (US); Tom Weisel, Ventura, CA (US); J. Terry Benson, West Hills, CA (US)

(73) Assignee: Depuy Mitek, Inc., New Brunswick, NJ (US)

( * ) Notice: Subject to any disclaimer, the term of this patent is extended or adjusted under 35 U.S.C. 154(b) by 587 days.

(21) Appl. No.: 10/831,441

(22) Filed: Apr. 22, 2004

(65) Prior Publication Data

US 2004/0199184 A1    Oct. 7, 2004

Related U.S. Application Data

(62) Division of application No. 10/255,523, filed on Sep. 25, 2002.

(60) Provisional application No. 60/326,287, filed on Oct. 1, 2001, provisional application No. 60/358,960, filed on Feb. 25, 2002.

(51) Int. Cl.
*A61B 17/06* (2006.01)

(52) U.S. Cl. ..................................... 606/223

(58) Field of Classification Search ........... 606/139, 606/144, 145, 222, 223, 224, 47, 49, 108, 606/114, 113, 110; 112/224, 221, 222, 98, 112/172, 198, 310; 223/102; D24/144–146; 119/801, 802; 163/1, 5, 6; 66/116–124
See application file for complete search history.

(56) References Cited

U.S. PATENT DOCUMENTS

| 1,037,864 | A | 9/1912 | Saxton |
| 1,449,087 | A | 3/1923 | Bugbee |
| 1,464,832 | A | 8/1923 | Richardson |
| 1,641,077 | A | 8/1927 | Fouquet |
| 3,090,386 | A | 5/1963 | Curtis |
| 3,349,772 | A | 10/1967 | Rygg |
| 3,393,687 | A | 7/1968 | Whitman |
| 3,470,875 | A | 10/1969 | Johnson |
| 3,807,407 | A | 4/1974 | Schweizer |

(Continued)

FOREIGN PATENT DOCUMENTS

DE    42 35 602 A1    4/1994

(Continued)

*Primary Examiner*—Todd E. Manahan
*Assistant Examiner*—Tuan V. Nguyen
(74) *Attorney, Agent, or Firm*—Myers Dawes Andras & Sherman LLP; Joseph C. Andras

(57) ABSTRACT

A suturing apparatus comprises a pair of jaws. A bendable needle housed in one of the jaws is adapted to carry a suture. An optional suture receiver may be disposed adjacent to the opposite jaw. A transition block curves the needle and directs it in a direction generally unparallel to an axis of the carrying jaw. The needle may also be configured to retrieve a suture. A retaining mechanism holds a suture in place to be engaged by the needle. The jaw housing the needle may include a lateral opening through which the suture may be inserted. The needle may also include a lateral notch which may be aligned with lateral opening to receive the suture. An actuator coupled to the needle enables the user to move the needle proximally to align the notch with the lateral slot.

8 Claims, 20 Drawing Sheets

U.S. PATENT DOCUMENTS

| | | |
|---|---|---|
| 3,842,840 A | 10/1974 | Schweizer |
| 3,901,244 A | 8/1975 | Schweizer |
| 3,946,740 A | 3/1976 | Bassett |
| 4,164,225 A | 8/1979 | Johnson et al. |
| 4,345,601 A | 8/1982 | Fukuda |
| 4,890,615 A | 1/1990 | Caspari et al. |
| 4,957,498 A | 9/1990 | Caspari et al. |
| 5,254,126 A | 10/1993 | Filipi et al. |
| 5,275,613 A | 1/1994 | Haber et al. |
| 5,318,577 A | 6/1994 | Li |
| 5,364,409 A | 11/1994 | Kuwabara et al. |
| 5,387,221 A | 2/1995 | Bisgaard |
| 5,397,325 A | 3/1995 | Della Badia et al. |
| 5,454,823 A | 10/1995 | Richardson et al. |
| 5,474,565 A * | 12/1995 | Trott .................. 606/144 |
| 5,478,345 A | 12/1995 | Stone et al. |
| 5,522,820 A | 6/1996 | Caspari et al. |
| 5,562,686 A | 10/1996 | Sauer et al. |
| 5,571,090 A | 11/1996 | Sherts |
| 5,632,751 A | 5/1997 | Piraka |
| 5,662,665 A | 9/1997 | Ludwick |
| 5,690,652 A | 11/1997 | Wurster et al. |
| 5,690,653 A | 11/1997 | Richardson et al. |
| 5,728,107 A | 3/1998 | Zlock et al. |
| 5,728,113 A | 3/1998 | Sherts |
| 5,730,747 A | 3/1998 | Ek et al. |
| 5,797,927 A | 8/1998 | Yoon |
| 5,824,009 A | 10/1998 | Fukuda et al. |
| 5,833,697 A | 11/1998 | Ludwick |
| 5,908,428 A | 6/1999 | Scirica et al. |
| 5,935,149 A | 8/1999 | Ek |
| 5,947,982 A | 9/1999 | Duran |
| 5,980,538 A | 11/1999 | Fuchs et al. |
| 6,051,006 A | 4/2000 | Shluzas et al. |
| 6,723,107 B1 * | 4/2004 | Skiba et al. ................. 606/144 |
| D523,554 S * | 6/2006 | Weisel ....................... D24/145 |
| D529,173 S * | 9/2006 | Weisel ....................... D24/145 |
| 7,112,208 B2 * | 9/2006 | Morris et al. ............... 606/144 |
| D530,421 S * | 10/2006 | Topper et al. ............. D24/145 |
| 2003/0220658 A1 | 11/2003 | Hatch et al. |
| 2003/0233106 A1 | 12/2003 | Dreyfuss |
| 2004/0010273 A1 | 1/2004 | Diduch et al. |

FOREIGN PATENT DOCUMENTS

| | | |
|---|---|---|
| EP | 0 778 004 A1 | 12/1995 |
| EP | 0 778 004 B1 | 12/1995 |

* cited by examiner

SUTURING APPARATUS AND METHOD

RELATED APPLICATIONS

This is a divisional application claiming the benefit of U.S. patent application Ser. No. 10/255,523 filed on Sep. 25, 2002, and entitled "Suturing Apparatus and Method," which claims the benefit of U.S. Provisional Application Ser. No. 60/326,287 filed on Oct. 1, 2001, entitled "SUTURING APPARATUS AND METHOD" and U.S. Provisional Application Ser. No. 60/358,960 filed on Feb. 25, 2002, entitled "SUTURING APPARATUS WITH RETAINING MECHANISM, all of which are fully incorporated herein by reference.

BACKGROUND OF THE INVENTION

1. Field of the Invention

The invention relates generally to suturing devices and methods.

2. Description of Prior Art and Related Information

Suturing apparatus in the past have been required to have an elongate configuration and a low profile facilitating their use through cannulas in less invasive surgery. These devices have typically included opposing jaws, which clamp on to the tissue to be sutured. Beyond this simple clamping motion, typically facilitated by scissor handles, the mechanism for threading a suture between the jaws and through the tissues have been exceedingly complex.

This complexity has derived primarily from the fact that the elongated, low profile configuration calls for an operating force that can be transmitted through an elongate tube. This force along the axis of the instrument must then be converted into a force extending generally perpendicular to the axis between the jaws. No simple structure has been devised to accommodate this transition. Furthermore, loading a suture onto a mechanism has also been complicated due to the complexity of the suturing mechanisms.

SUMMARY OF THE INVENTION

In accordance with the present invention, structures and associated methods are disclosed which address these needs and overcome the deficiencies of the prior art.

In one aspect, a suturing apparatus comprises a first jaw and a second jaw movable with respect to each other. A bendable needle is carried by the first jaw and adapted to carry a suture. The needle is movable between a first position wherein the needle is substantially housed within the jaw and a second position wherein a distal portion of the needle protrudes from the first jaw. The apparatus further comprises means for securing the suture in place prior to being carried by the bendable needle, and a suture receiver spaced apart from the first jaw and configured to disengage the suture carried by the bendable needle.

The securing means may comprise a cantilevered spring included in a distal portion of the first jaw, a groove defined in a distal portion of the first jaw, a flap, or an elastomeric pad. The first jaw defines an axis and further comprises a transition block adapted to guide the bendable needle in a direction substantially perpendicular to the axis.

In another aspect, a suturing apparatus comprises a first jaw defining an ingress, a second jaw movable with respect to the first jaw, and a bendable needle carried by the first jaw and movable between a proximal position and a distal position. The needle defines a needle slot that may be aligned with the ingress to enable loading of a suture through the ingress into the needle slot.

The apparatus further comprises a suture receiver, which may be disposed adjacent to the second jaw, or integral with the second jaw. The apparatus further comprises an actuator coupled to the bendable needle and configured for moving the bendable needle between the proximal position and the distal position. The actuator preferably comprises a thumb lever. The first jaw defines an axis and further comprises an axial slot in communication with the ingress. The ingress may comprise a lateral opening, and the needle slot may comprise a lateral slot.

A suture retrieving apparatus is also provided. The suture retrieving apparatus comprises a first jaw and a second jaw movable with respect to each other, a suture receiver spaced apart from the first jaw, the suture receiver being adapted to releasably retain a suture, and a bendable needle carried by the first jaw. The bendable needle is movable between a proximal position and a distal position. The bendable needle has a distal needle portion adapted to engage with the suture when the bendable needle is in the distal position. The distal needle portion comprises a hook. The second jaw may comprise the suture receiver.

A method is provided for suturing a tissue. The method comprises the steps of clamping a piece of tissue to be sutured, securing a suture in place for engagement with a bendable needle, engaging a suture with a bendable needle, carrying the suture toward a receiver with the bendable needle, retaining the suture with the receiver, and retracting the bendable needle to release the suture.

The step of clamping a tissue to be sutured comprises the step of capturing the piece of tissue with a first jaw and a second jaw. The method further comprises the step of advancing the bendable needle in an axial direction.

The step of carrying the suture toward a receiver with the bendable needle comprises the step of bending the bendable needle, and moving at least a portion of the bendable needle in a transverse direction.

A method is also provided for loading a suture onto a suturing apparatus. The method comprises the steps of housing a needle with a needle slot in a first jaw, biasing the needle in a distal direction with respect the first jaw so that the needle slot is not aligned with an ingress of the first jaw, aligning the needle slot with the ingress, disposing a suture through the ingress into the needle slot; and releasing the biased needle such that the needle engages the suture and carries the suture distally.

The step of aligning the needle slot with the ingress may comprise the step of moving the needle either proximally or distally. The step of moving the needle proximally comprises moving the needle proximally with a finger slide. The step of disposing a suture through the ingress into the needle slot comprises looping the suture about the ingress.

In summary, a suturing apparatus comprises a pair of jaws. A bendable needle housed in one of the jaws is adapted to carry a suture toward a suture receiver disposed adjacent to the opposite jaw. A transition block curves the needle and directs it in a direction generally not parallel to an axis of the carrying jaw. The needle may also be configured to retrieve a suture. A retaining mechanism holds a suture in place to be engaged by the needle. The jaw housing the needle may include a lateral opening through which the suture may be inserted. The needle may also include a lateral notch, which may be aligned with lateral opening to receive the suture. An actuator coupled to the needle enables the user to move the needle proximally to align the notch with the lateral slot.

The invention, now having been briefly summarized, may be better visualized by turning to the following drawings wherein like elements are referenced by like numerals.

The invention and its various embodiments can now be better understood by turning to the following detailed description wherein illustrated embodiments are described. It is to be expressly understood that the illustrated embodiments are set forth as examples and not by way of limitations on the invention as ultimately defined in the claims.

DETAILED DESCRIPTION OF THE PREFERRED EMBODIMENTS AND BEST MODE OF INVENTION

Figure 1:
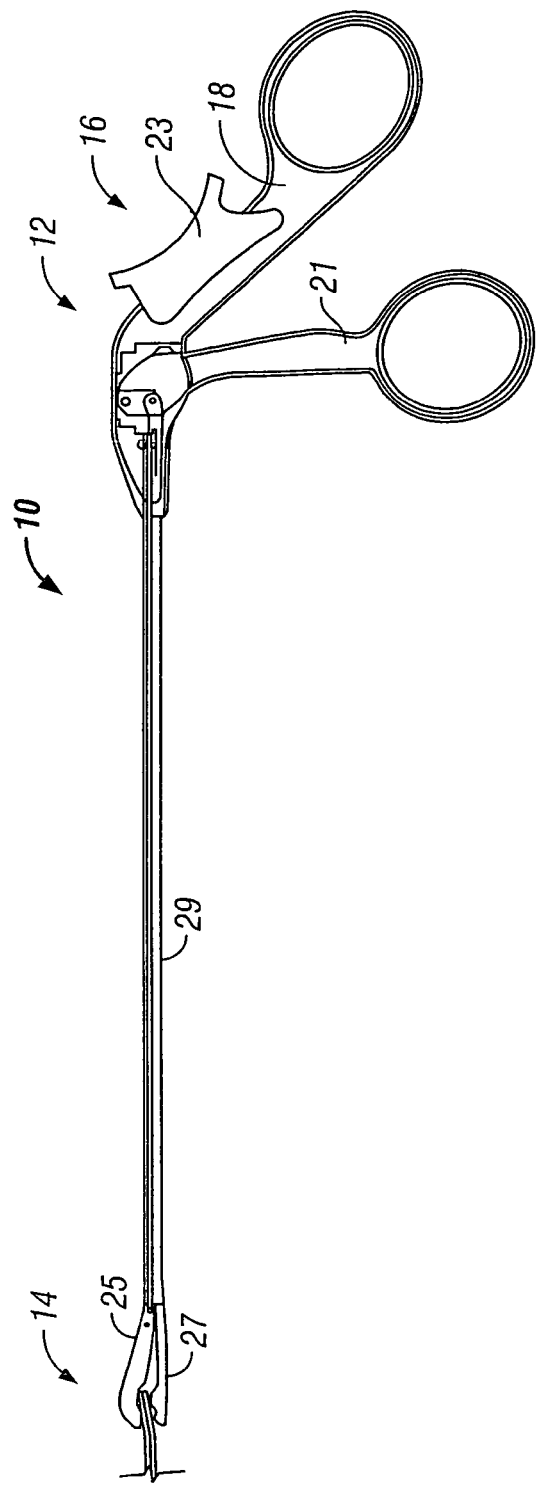
FIG. 1 is a side elevation view of a first preferred embodiment of a suturing apparatus according to the invention.
Figure 2:
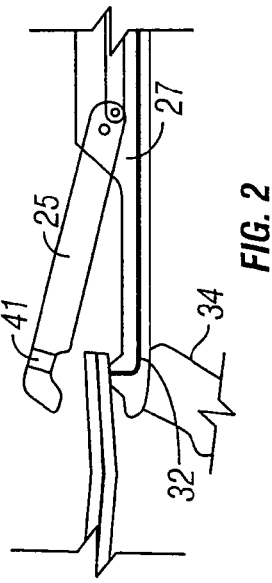
FIG. 2 is a close-up view of the first preferred suturing apparatus showing a bendable needle substantially housed within a lower jaw.

A first preferred embodiment of a suturing apparatus is illustrated in FIG. 1 and designated generally by the reference numeral 10. The apparatus 10 is illustrated to have an elongate configuration with a proximal end 12 and a distal end 14. A handle assembly 16 is disposed at the proximal end 12 and includes scissor handles 18 and 21 as well as an actuator 23. A pair of opposing jaws 25 and 27 are disposed at the distal end and are coupled to the handle assembly 16 through an elongate shaft or tube 29. In one embodiment, the upper jaw 25 is pivotal with respect to the lower jaw 27 as illustrated in FIG. 2.

Figure 3:
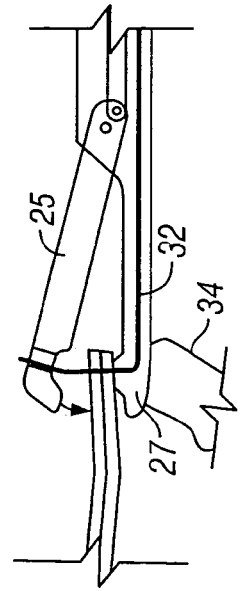
FIG. 3 is a close-up view of the first preferred suturing apparatus showing the bendable needle piercing a piece of tissue.

In the illustrated embodiment the lower jaw 27 includes a needle 32 of particular interest to the present invention. In this case, the needle 32 includes a body having a generally flat, narrow and elongate configuration. As shown in FIGS. 1-3, the needle 32 is formed from a bendable material so that it can be moved generally with an axial force provided, for example, by a user's thumb, and can be bent on a curve, for example, to 90°, to move generally perpendicular to the axis and toward the opposing upper jaw 25. It is to be expressly understood that the needle 32 can be substantially straight, as shown in FIG. 1, and then be bent at any angle and advanced in any direction away from the axis. The actuator 23, which preferably comprises a thumb rocker or slide, is coupled to the needle 32. The actuator 23 enables a user to advance the needle 32 distally to a protruding, operative position and proximally to a retracted, inoperative a position.

Figure 4:
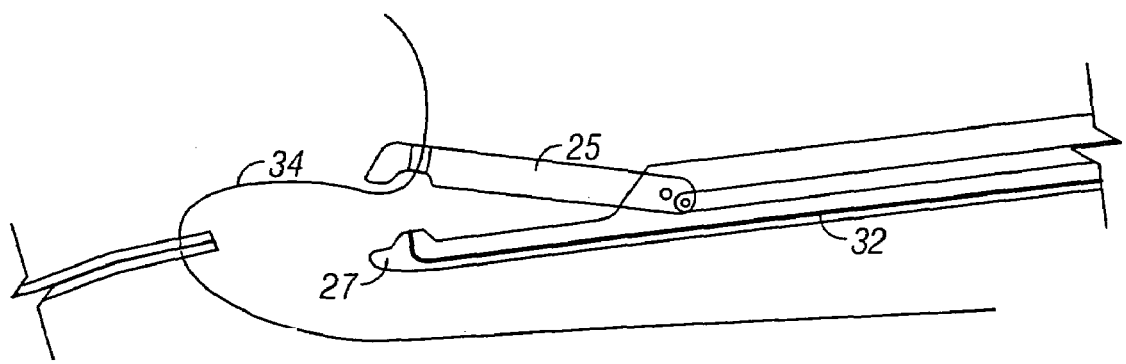
FIG. 4 is a close-up view of the first preferred suturing apparatus removed from the piece of tissue.

Threading this needle 32 with a suture 34 enables the needle to be deployed through the tissue and to carry with it the suture 34 to be threaded. The opposing jaw 25 may include an optional receiver, which is adapted to remove the suture from the needle 32 as the needle 32 is withdrawn back into the lower jaw 27. At this point, the suture extends through the tissue and into the upper jaw. Removal of the jaws from the tissue, as illustrated in FIG. 4 permits withdrawal of the apparatus 10 leaving the suture in place for tying or further manipulation. A suture receiver is optional since the tissue itself may frequently serve as a receiver for the suture once the needle is retracted.

Figure 5A:
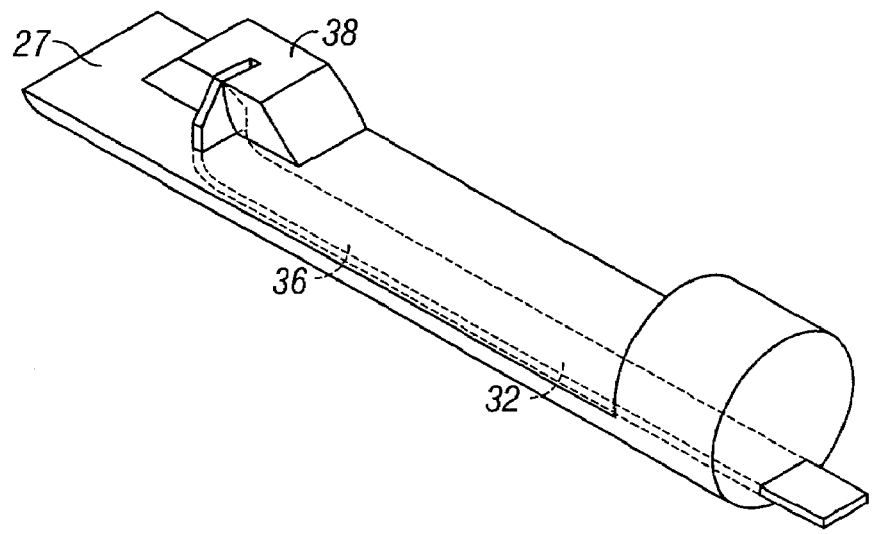
FIG. 5A is a perspective view of a jaw of the first preferred suturing apparatus housing the bendable needle.
Figure 5B:
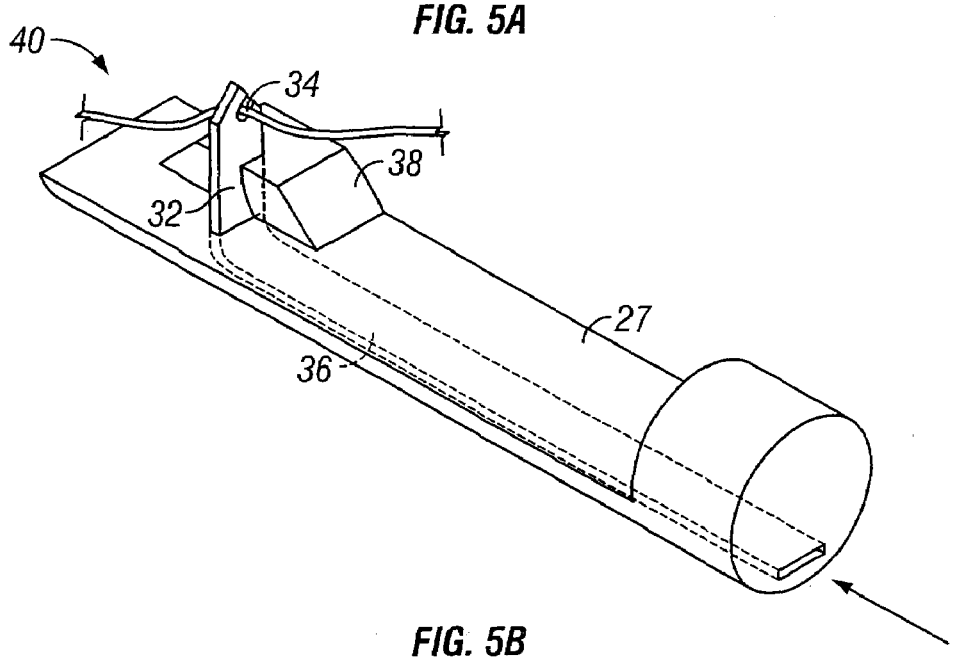
FIG. 5B is a perspective view of the jaw of FIG. 5A showing the bendable needle advanced to a distal, piercing position.

In this embodiment, the lower jaw is illustrated in FIG. 5A to include an elongate configuration and a channel 36 adapted to receive the needle 32. The needle is bent at the distal end of this jaw 27 and up through a transition block 38 which aides in curving the needle 32 and directing it toward a suture receiver. Though the illustrated embodiment shows the transition block 38 curving the needle 32 perpendicularly with respect to the axis of the lower jaw 27, the transition block 38 may be configured to curve and direct the needle 32 at any particular angle or direction that is generally unparallel to the axis of the lower jaw 27. FIG. 5A shows the needle retracted and FIG. 5B shows the needle 32 deployed and provided with a slot 40 to carry the suture 34 to the opposing jaw 25. This configuration is further illustrated in the radial cross-section view of FIG. 6.

Figure 7A:
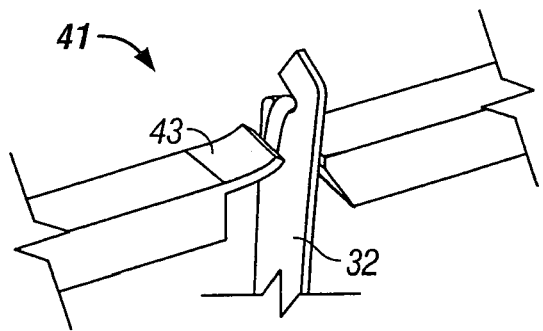
FIG. 7A is an operative view illustrating a preferred suture receiver intercepting the suture carried by the needle.
Figure 7B:
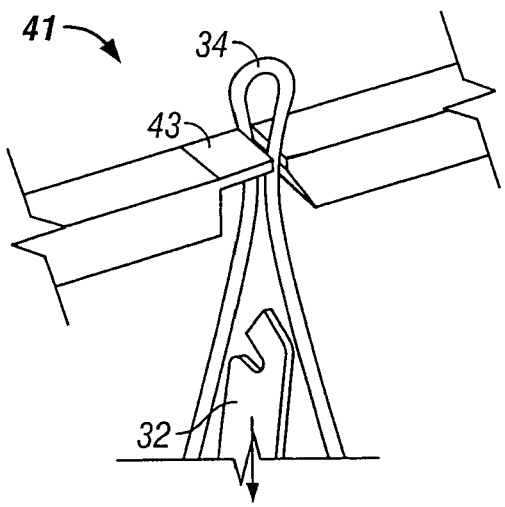
FIG. 7B is a perspective view of the preferred suture receiver of FIG. 7A retaining the suture after the needle is retracted.

In the upper jaw 25, a suture receiver 41 is provided to remove the suture 34 from the needle 32. A metal or elastomeric flap, or paddle, 43 is provided to engage the needle 32 and threaded suture 34 as illustrated in FIG. 7A. This flap 43 forces the suture 34 from the needle slot 40 as the needle 32 is withdrawn as illustrated in FIG. 7.

Figure 8A:
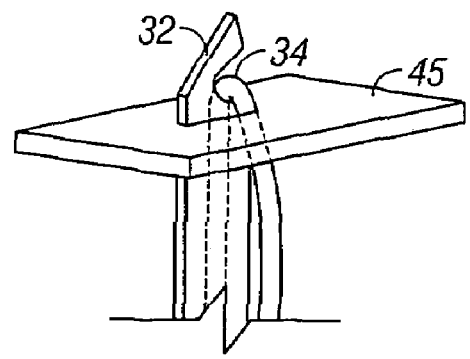
FIG. 8A is an operative view of a further preferred suture receiver.
Figure 8B:
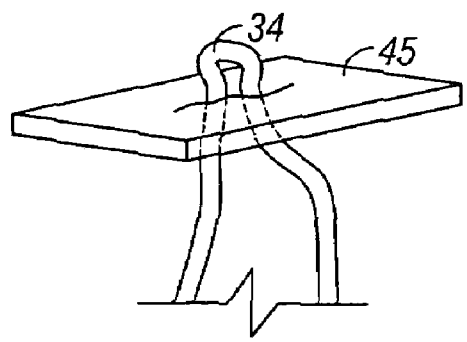
FIG. 8B is an operative of the preferred suture receiver of FIG. 8A retaining the suture after the needle is retracted.

In a similar embodiment, the needle 32 and threaded suture 34 is forced through an elastomeric pad 45 which similar engages the suture 34 and removes it from the needle slot 40 as the needle 32 is withdrawn as illustrated in FIG. 8B.

Figure 6:
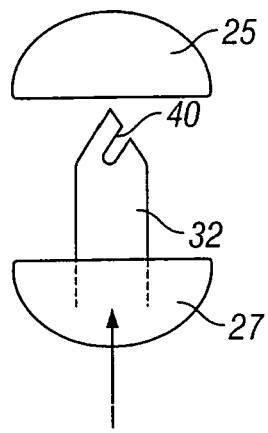
FIG. 6 is a front end view of the first preferred suturing apparatus.
Figure 9:
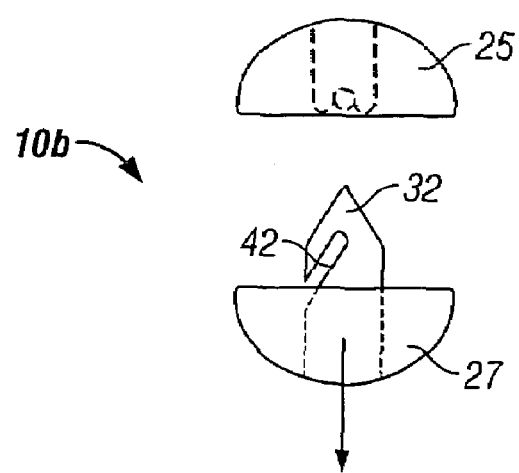
FIG. 9 is a front-end view of a second preferred embodiment of a suture apparatus comprising a suture-retrieving device.
Figure 10A:
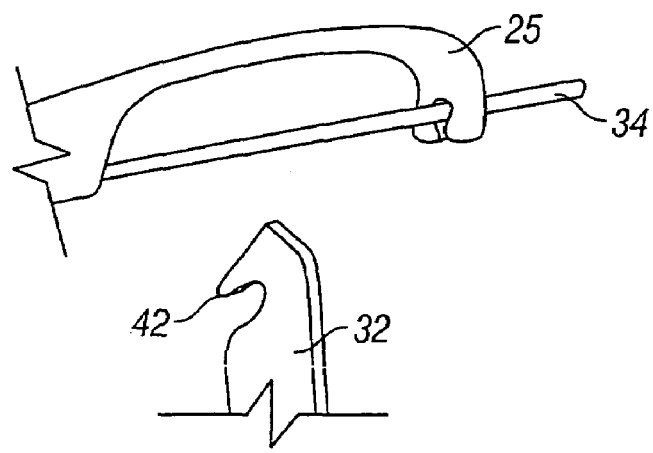
FIG. 10A is an operative view of the preferred suturing retrieving device of FIG. 9.
Figure 10B:
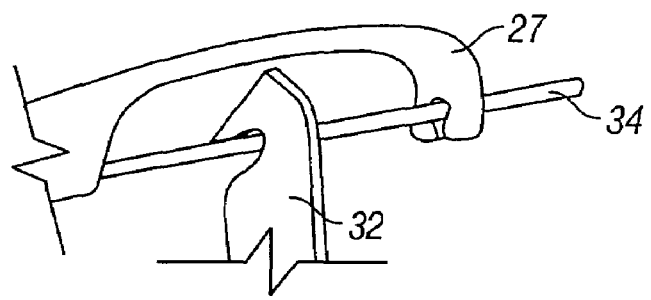
FIG. 10B is an operative view of the preferred suturing retrieving device showing a retrieving needle engaging a suture.
Figure 10C:
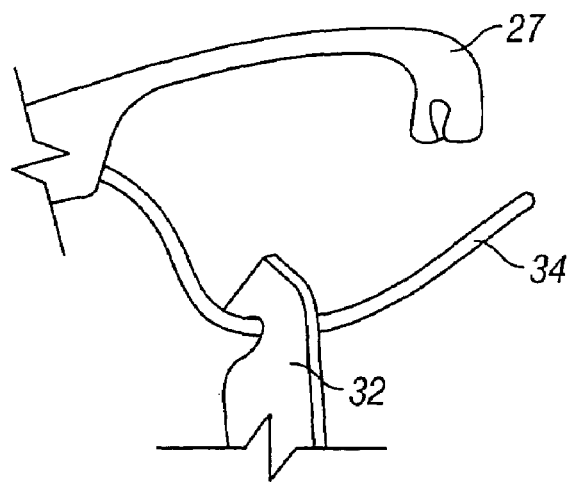
FIG. 10C is an operative view of the preferred suturing retrieving device showing the needle retrieving the suture.

A second preferred embodiment of a suturing apparatus is illustrated in FIG. 9 which is a cross-section view similar to FIG. 6, but showing a needle 32 which functions as a retriever rather than a carrier. In this embodiment, the suture 34 is initially carried by the upper jaw 25. A needle slot 42 in this case extends distally from the side of the needle 32. When this needle 32 and slot 42 are extended, as illustrated in FIG. 10A, the slot 42 engages the suture 34 in the upper jaw 25. As the needle 32 is withdrawn, the suture is retrieved in the needle slot 42 and carried back through the tissue. The final step in this process is the same as previously discussed with reference to FIG. 4.

Figure 11:
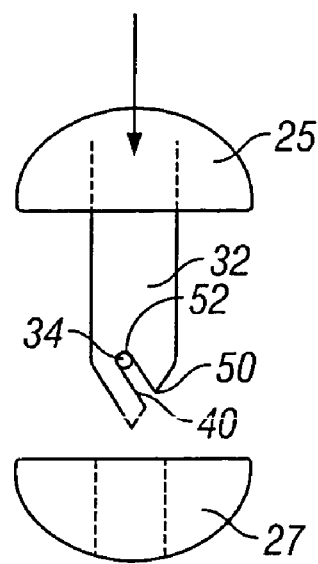
FIG. 11 is a front-end view of a third preferred suturing apparatus wherein a bendable needle is carried by an upper jaw.

It will be apparent that this apparatus 10 could also operate with the needle 32 carried by the upper jaw 25. Such a feature is shown in a third preferred embodiment illustrated in the cross-sectional view of FIG. 11 where the needle 32 functions as a suture carrier. In particular, a suture slot 40 defined in the needle 32 comprises an opening 50 that is located distally to an end 52 such that the slot 40 faces the receiver, or lower jaw 27. A suture 34 is thus carried by the needle 32 toward the opposing, lower jaw 27.

Figure 12:
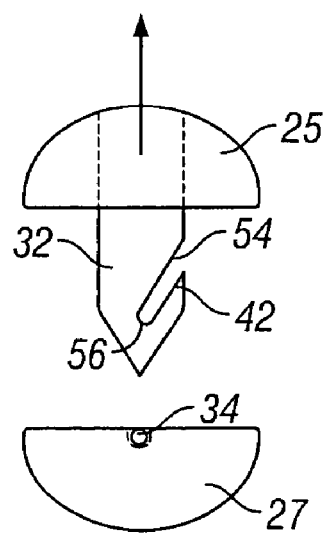
FIG. 12 is a front-end view of a fourth preferred suture retrieving apparatus wherein a bendable needle is carried by an upper jaw.

In FIG. 12, a fourth preferred embodiment of a suturing apparatus comprises a suture-retrieving device wherein the needle 32 is carried by the upper jaw 25. In this case, the needle 32 functions as a retriever of the suture 34. The needle 32 defines a slot 42 with an opening 54 that is located proximally to an end 56 such that the slot 42 faces away from the opposing, lower jaw 27. In the illustrated embodiment, a distal portion of the needle 32 is thus preferably shaped as a hook.

Figure 13:
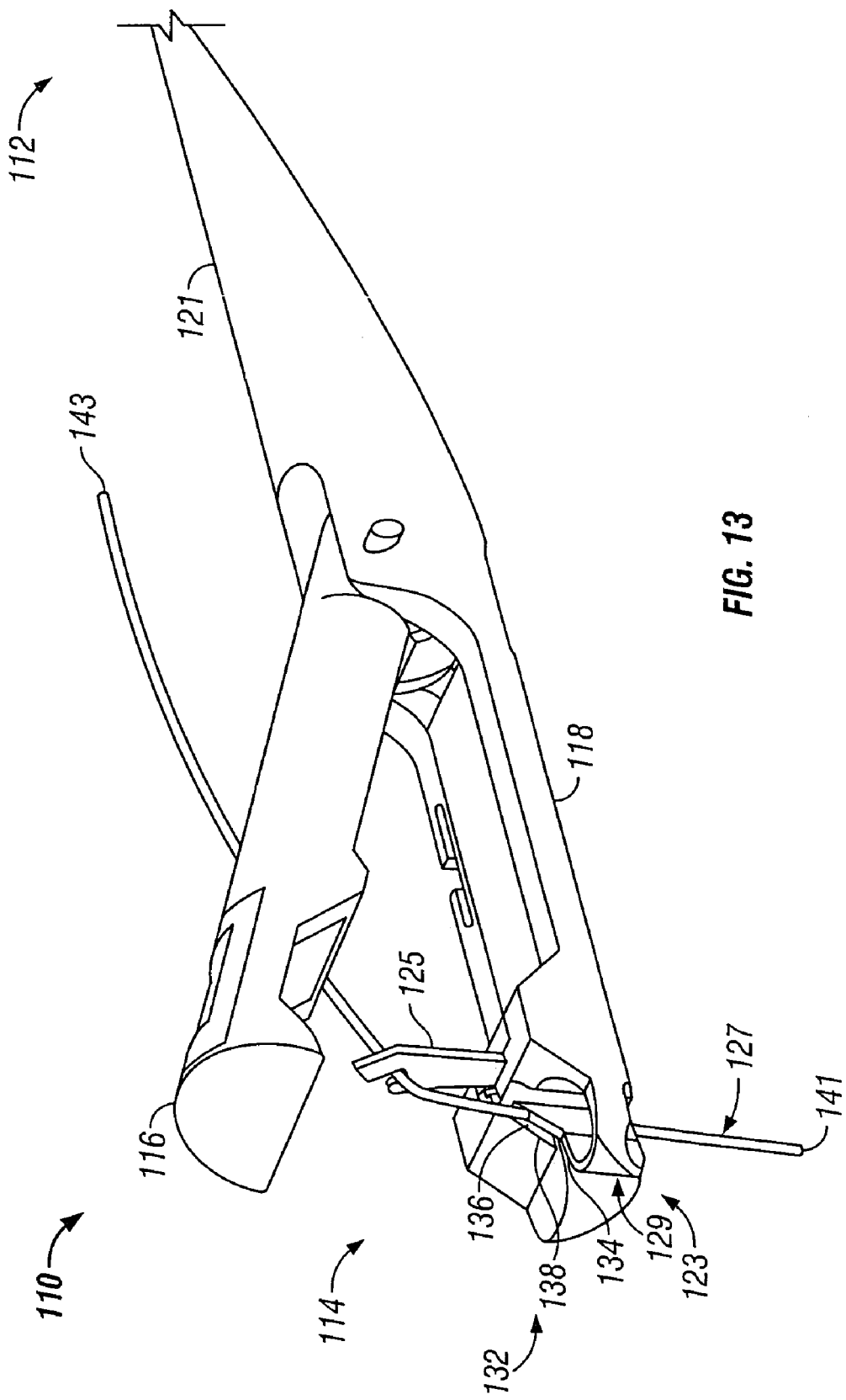
FIG. 13 is a perspective view of a fifth preferred suturing apparatus including a securing mechanism.
Figure 14:
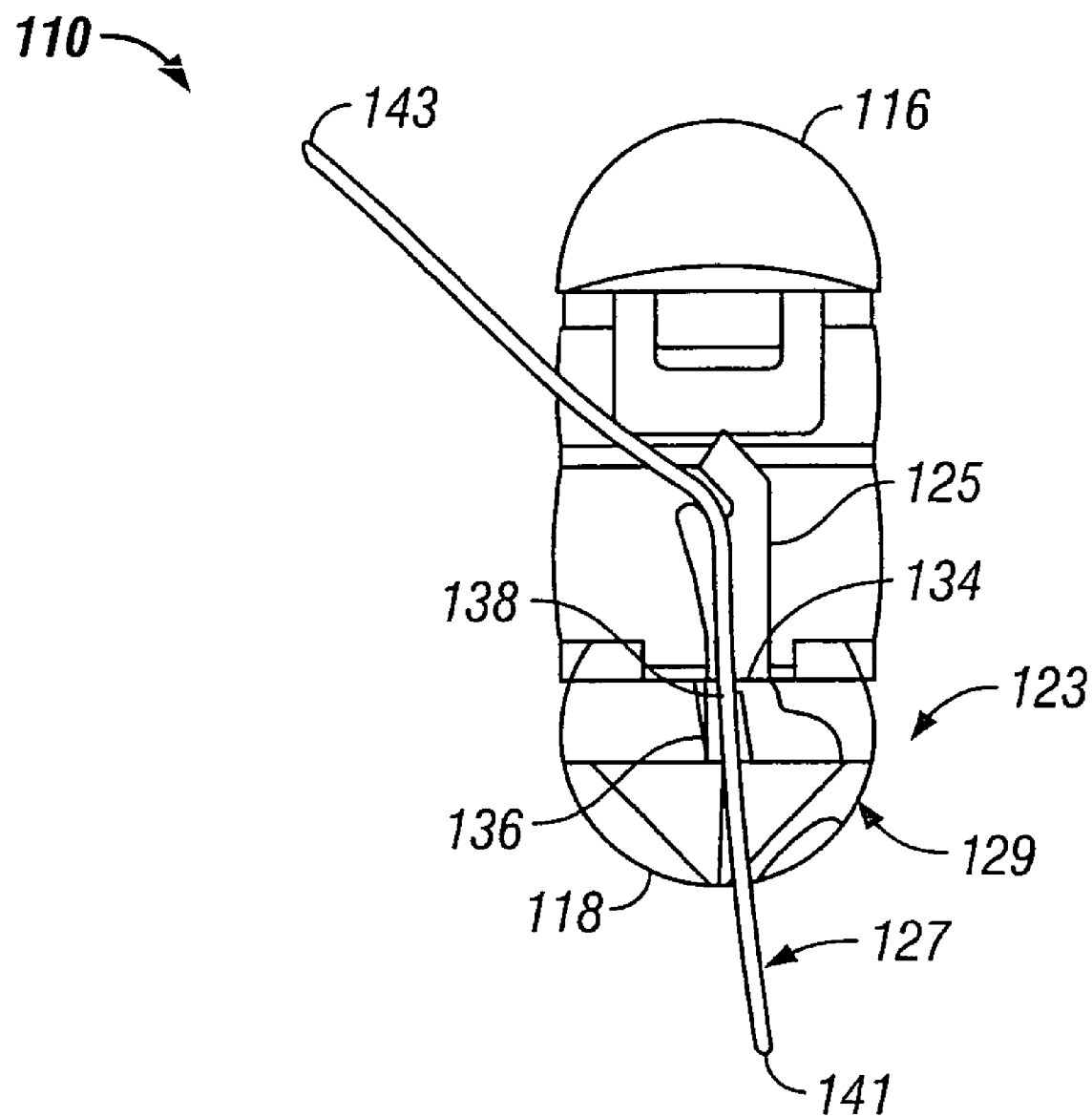
FIG. 14 is a front-end view of the fifth suturing apparatus.
Figure 15:
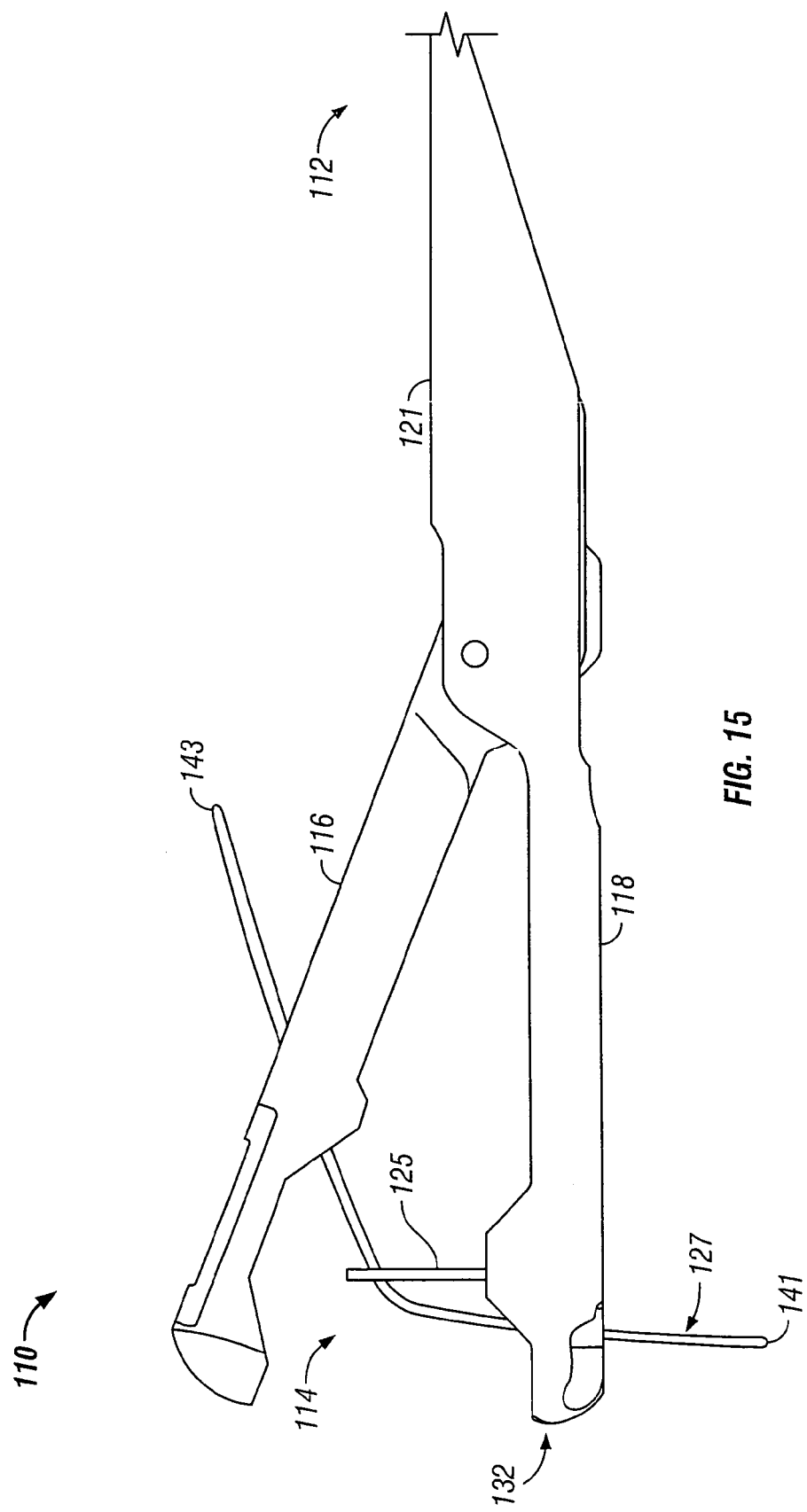
FIG. 15 is a side elevation view of the fifth suturing apparatus.

A fifth preferred embodiment of a suturing apparatus is illustrated in FIG. 13 and designated generally by the reference numeral 110. In FIGS. 13-15, the apparatus 110 includes an elongate configuration with a proximal end 112 and a distal end 114. A handle assembly (not shown) is disposed at the proximal end 112 and may include scissor handles, which are operatively coupled to a pair of opposing suturing jaws 116 and 118 at the distal end 114. An elongate shaft or tube 121 couples the jaws 116, 118 to the handle assembly. In one embodiment, the upper jaw 116 is pivotal with respect to the lower jaw 118 as illustrated in FIG. 13-15.

In the illustrated embodiment, the lower jaw 118 includes a retaining mechanism 123 of particular interest to the present invention. The apparatus 110 may include a handle assembly, a bendable needle 125 housed in one of the jaws 116, 118, and a suture receiver included in the other of the jaws 116, 118 as described above. Since the retaining mechanism 123 serves to securely hold a suture 127 while easily permitting its release when engaged by the needle 125, the mechanism 123 is preferably included in the jaw that houses the needle 125. For example, if the needle 125 is housed in the upper jaw 116, then the retaining mechanism 123 would also be included in the upper jaw 116.

Figure 16:
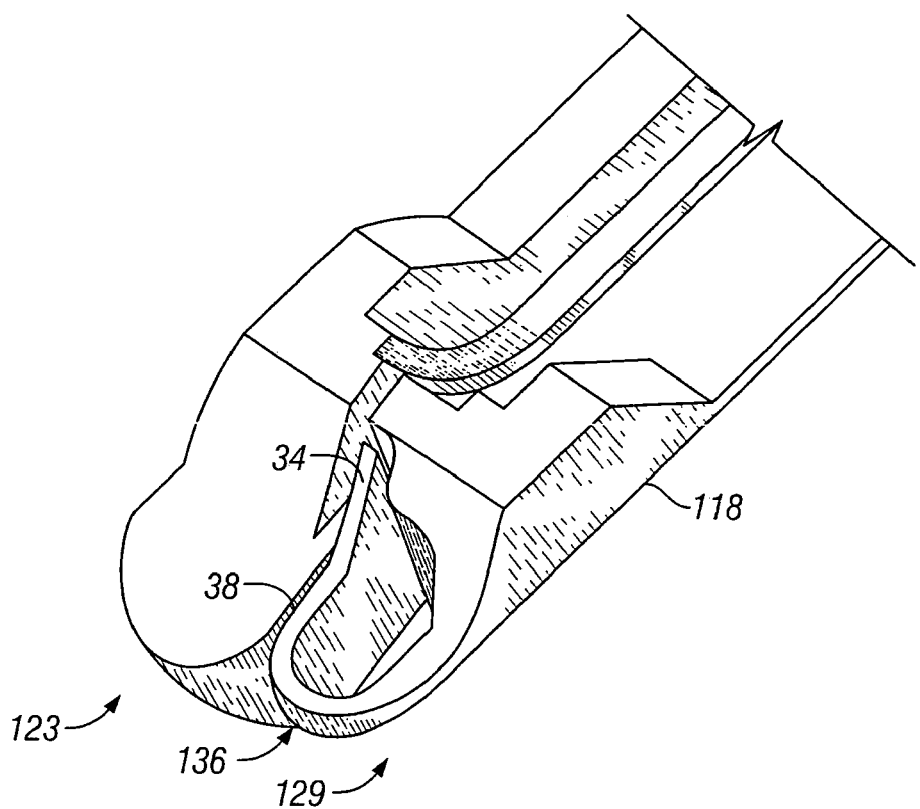
FIG. 16 is a close-up, perspective view of a suturing jaw incorporating the securing mechanism.
Figure 17:
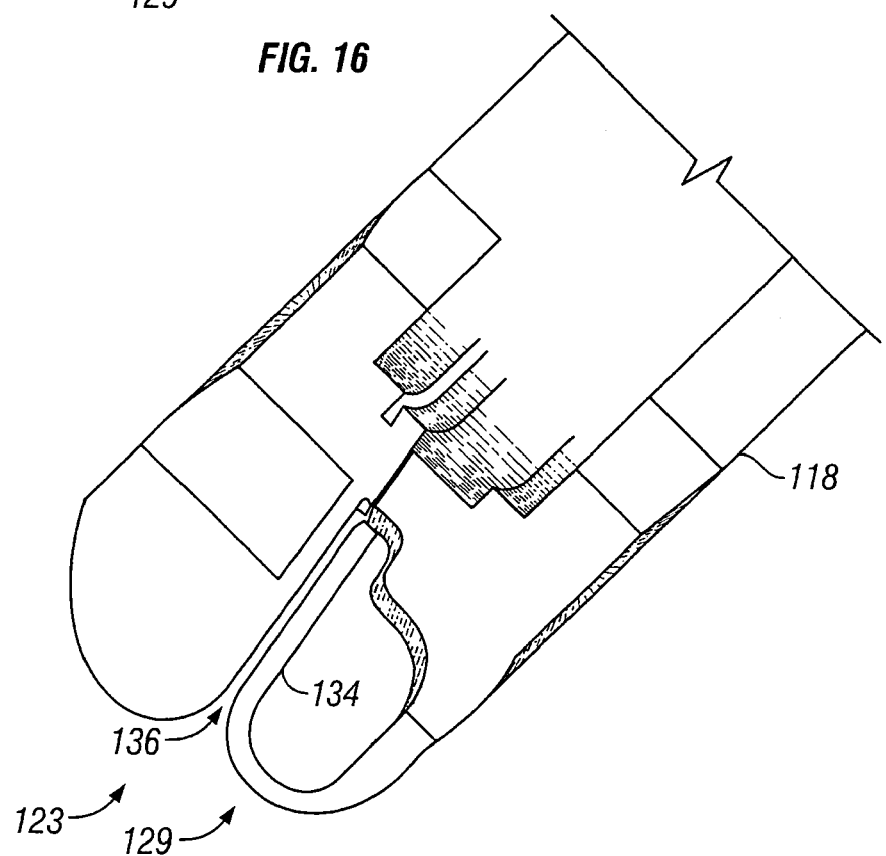
FIG. 17 is a top plan view of a tip of the suturing jaw of FIG. 16.

A first preferred securing mechanism 123 comprises a spring 129 formed at a distal tip 132 of the jaw 118. The spring 129 includes a cantilever portion 134 bent back on itself. A wedge, or groove, 136 is defined between the cantilever portion 134 and an opposite wall 138 as shown more clearly in FIGS. 16 and 17. In the illustrated embodiment of FIGS. 13-16, the securing mechanism 123 is formed integrally with the jaw 118. To assemble the suture 127, a first end 141 is held beneath the jaw 118 and the other end 143 above the jaw 118. The ends 141, 143 may be pulled in a proximal direction such that the suture 127 is wedged into the groove 136. When disposed in the groove 136, the cantilever portion 134 biases the suture 127 against the opposite wall 138, thus pinching the suture 127 securely in place for engagement by the needle 125.

The biasing force of the spring 129 is configured such that the suture 127 is both held securely absent engagement by the needle 125, and yet is permitted to be easily released upon engagement. It is to be expressly understood, therefore, that the spring 129 may comprise a variety of mechanisms capable of abutting, or pinching, the suture 127 against an opposing surface while permitting its release upon engagement with a needle. The groove 136 is preferably aligned with or disposed adjacent to a needle exit port 145 such that when the ends 141, 143 are tugged proximally, a portion 147 of the suture 127 lies along the path of the transversely extending needle 125.

Figure 18:
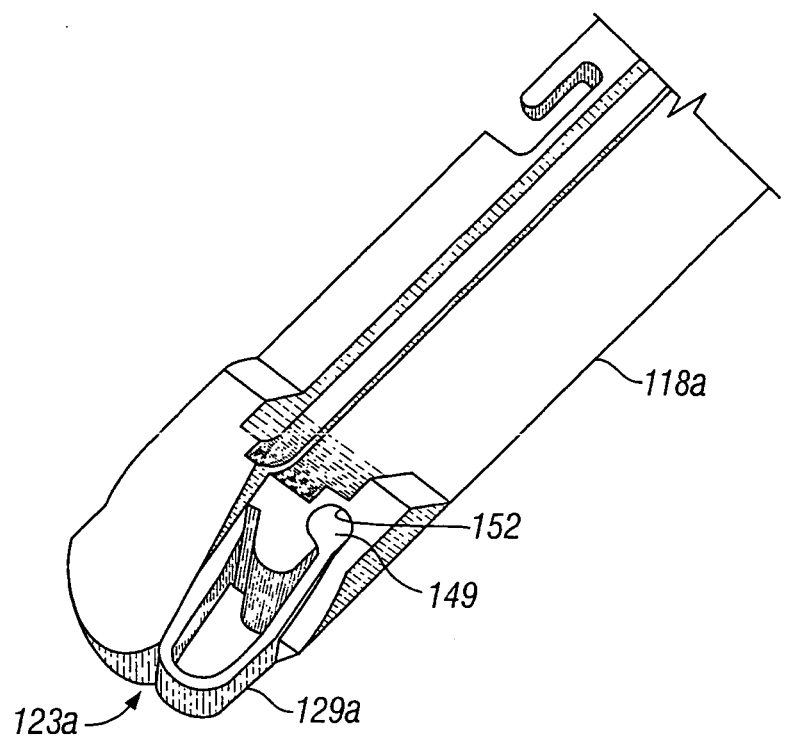
FIG. 18 is a perspective view of a suturing jaw incorporating an alternative securing mechanism.

In FIG. 18, a second preferred retaining mechanism 123a may include a spring mechanism 129a formed separately from the jaw 118a. The spring mechanism 129a includes an anchor 149 configured to fit within a slot 152 defined in the jaw 118a.

Figure 19:
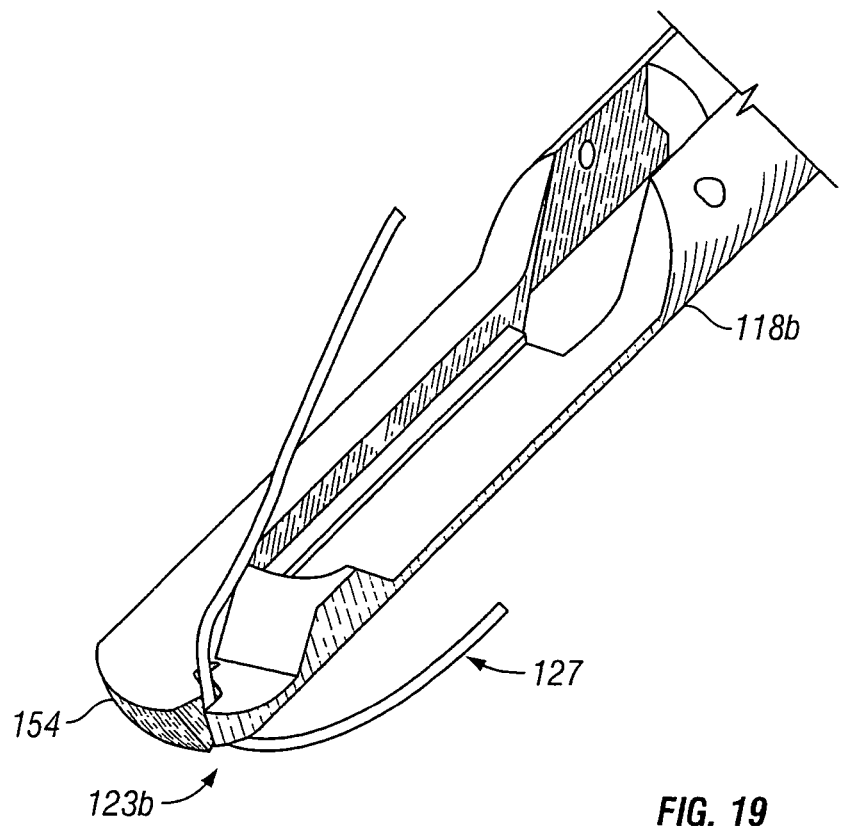
FIG. 19 is a close-up perspective of a suturing jaw incorporating a further alternative securing mechanism.
Figure 20:
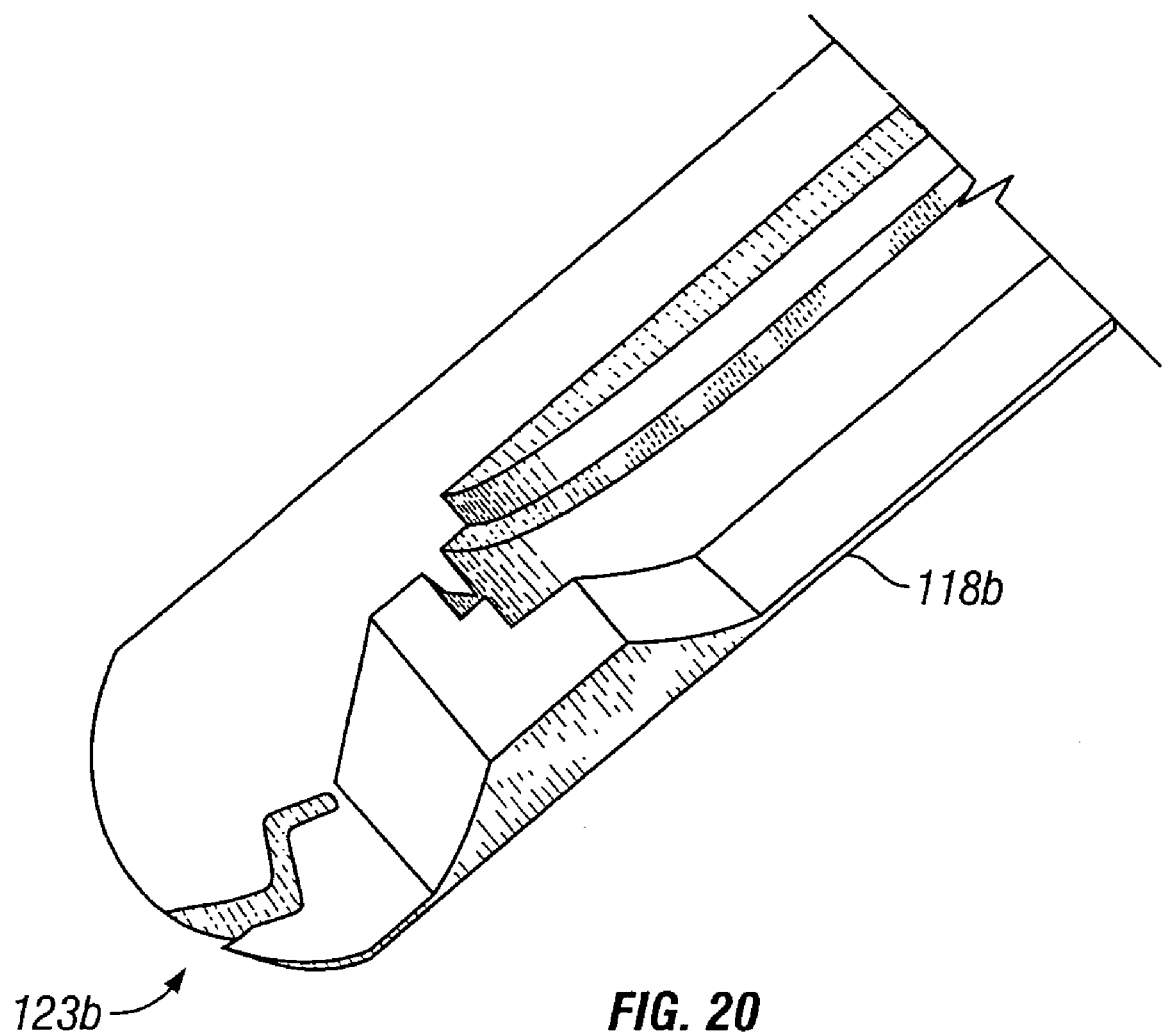
FIG. 20 is a perspective view of the suturing jaw of FIG. 19.

In FIGS. 19 and 20, a third preferred retaining mechanism 123b comprises a zigzag groove 154 that becomes increasingly narrow as it extends proximally. The zigzag pattern in combination with the proximal tapering facilitates a tight fit when the suture 127 is drawn proximally. In particular, the proximally tapered configuration of the groove 154 pinches the suture in place as it drawn proximally while the zigzag pattern prevents the suture 127 from being distally disengaged from the jaw 118b.

Figure 21:
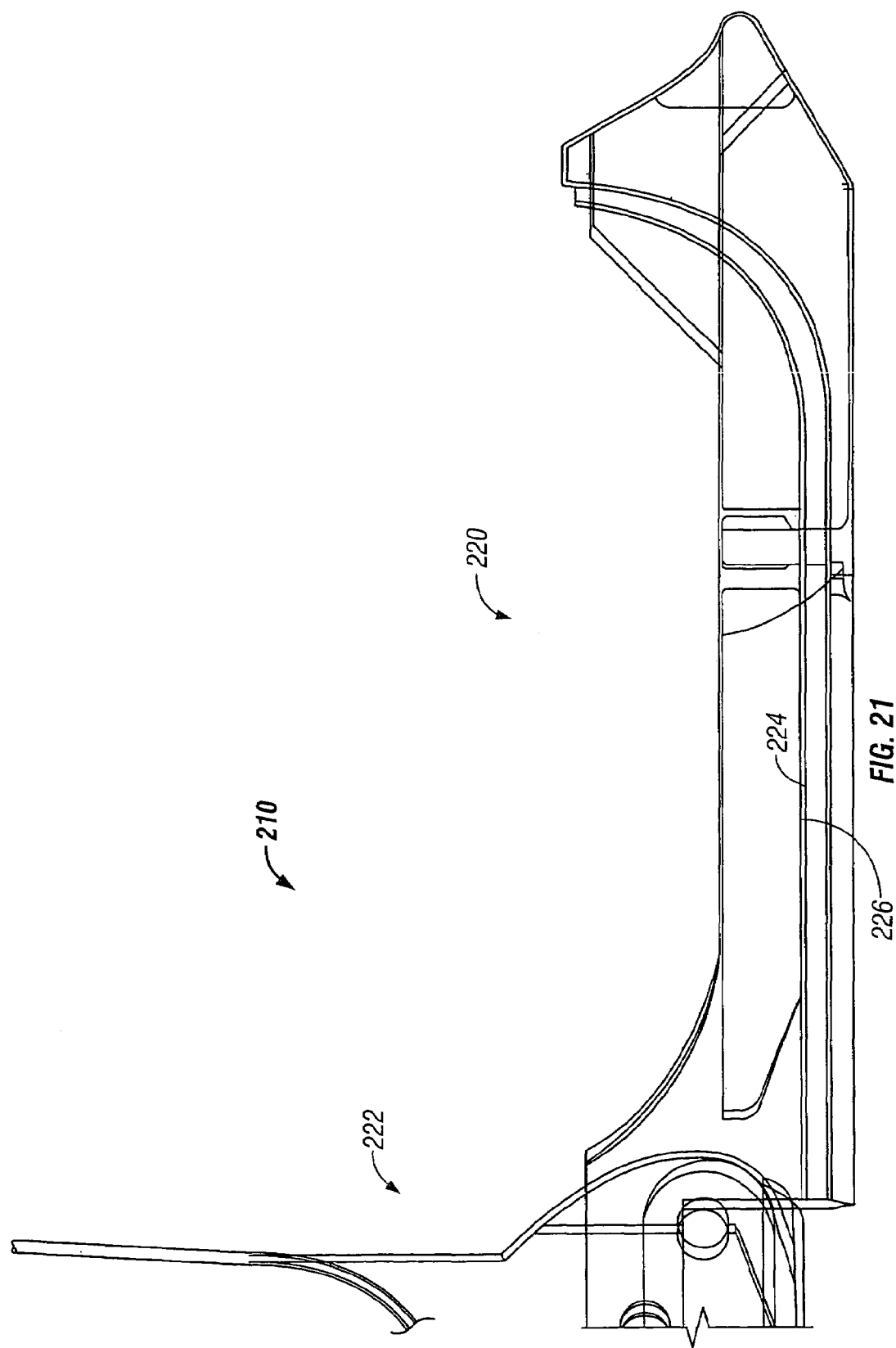
FIG. 21 is a partially removed side elevation view of a sixth preferred suturing apparatus.
Figure 22:
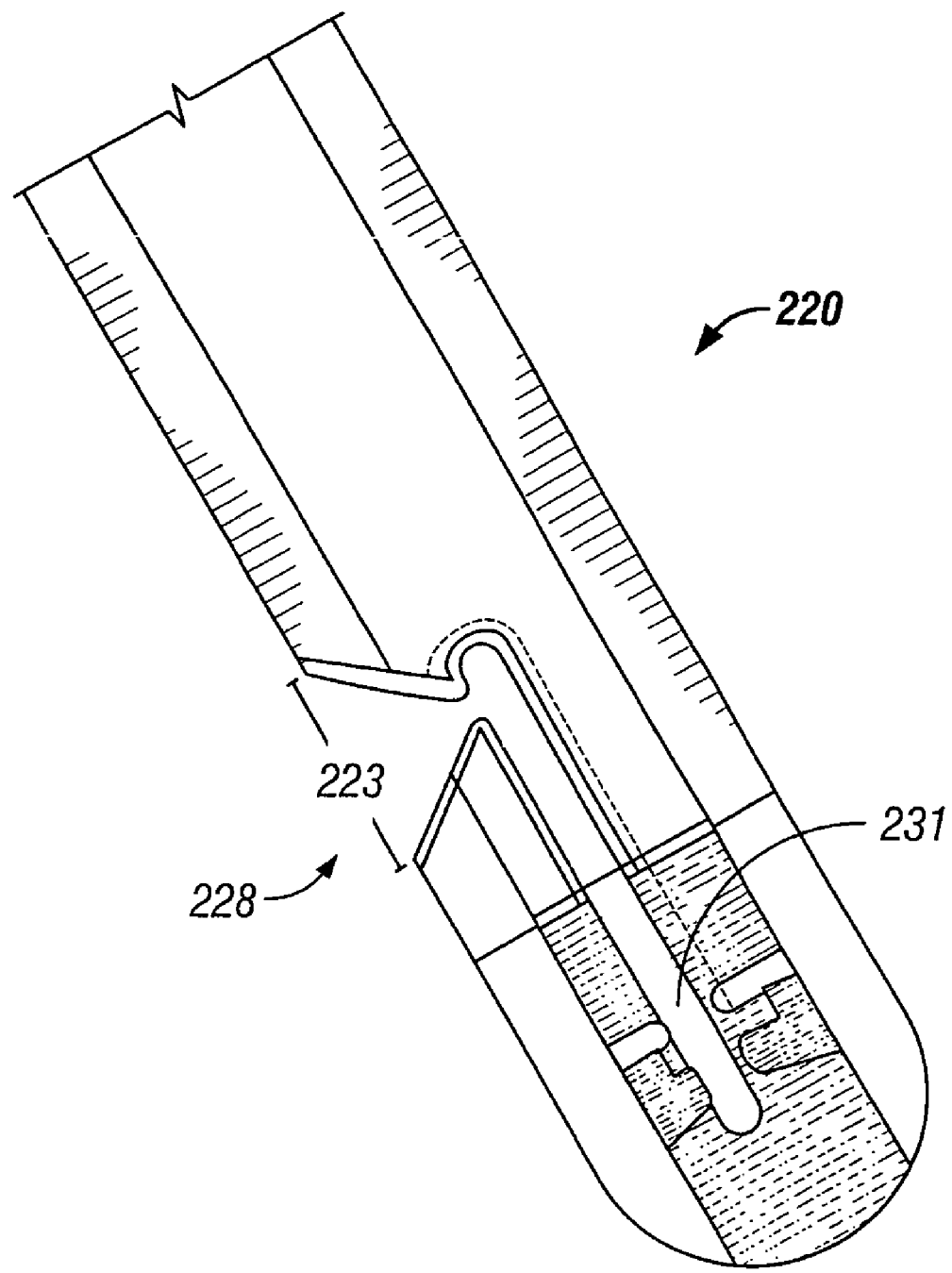
FIG. 22 is a top plan view of a needle carrying jaw of the sixth preferred suturing apparatus.
Figure 23:
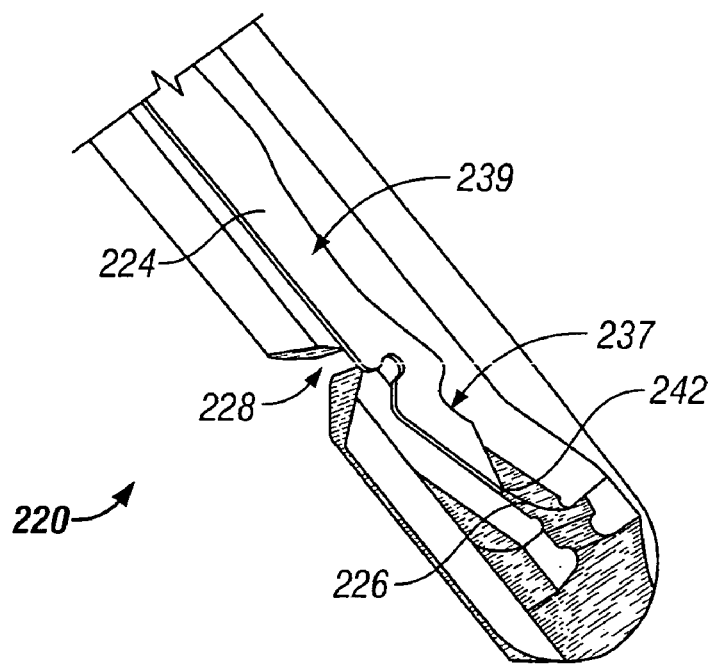
FIG. 23 is a perspective view of the needle carrying jaw of FIG. 22 with a bendable needle shown overlaid for clarity.

A sixth embodiment of a suturing apparatus is shown in FIGS. 21-27 and designated generally by the reference numeral 210. The apparatus 210 comprises a first jaw 220 and a second jaw 222 that are pivotal with respect to each other. In FIGS. 21-23, the first jaw 220 is configured to house a bendable needle 224. This needle carrying jaw 220 may comprise either the lower or upper jaw of the apparatus 210. The bendable needle 224 is substantially disposed in a channel 226 within the first jaw 220 when the needle 224 is in a non-operative, or non-piercing, position.

In FIG. 22, the first jaw 220 defines an opening, or ingress 228, that is in communication with an axial slot 231. The ingress 228 is preferably provided with a relatively wide mouth 233 is open to one of the sides of the first jaw 220. This preferably lateral ingress 228 tapers as it approaches the axial slot 231.

In FIG. 23, the needle 224 of particular interest to the invention is shown out of position, overlaying the first jaw 220 for clarity. When assembled, the needle 224 would reside in the channel 226 as discussed above. The needle 224 comprises a lateral slot, or notch 235 (see FIG. 28). An edge defining the notch 235 is preferably radiused, or smoothed, such it would not cut a suture. As best shown in original FIG. 28. the needle 224 comprises distal portions that define a sharp needle tip 242, notch or slot portions that define the notch or slot 235 and its associated opening, and first and second void portions that define a first distal crescent-shaped void 237 and an adjacent second proximal crescent-shaped void 239. In the preferred needle of original FIG. 28, the distal portions that define the sharp needle tip 242 are equally bifurcated by the needle's axis. As further shown in FIG. 28, the slot portions defining the slot 235 define a base and a channel extending laterally of the base, the preferred base being configured as a circle with a diameter that is greater than a width of the channel. The voids 237, 239 collectively provide flexibility that is spread out on either side of the notch 235, over a greater length of the needle 224, such that all stresses do not collect at the notch 235 when the needle 224 is bent. The notch 235 is preferably disposed between the voids 237, 239. As further shown in original FIG. 28, the first void 237 is shaped like a crescent with a first radius and a first axial length and the second void 239 is shaped like a crescent with a second radius greater than the first radius and with a second axial length greater than the first axial length.

Figure 24:
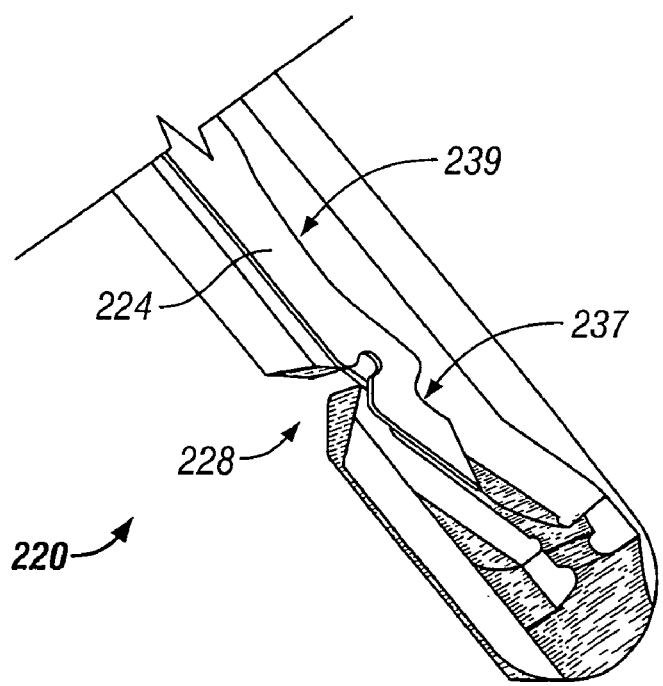
FIG. 24 is a perspective view of the needle carrying jaw with the bendable needle shown overlaid in an aligned position.
Figure 25:
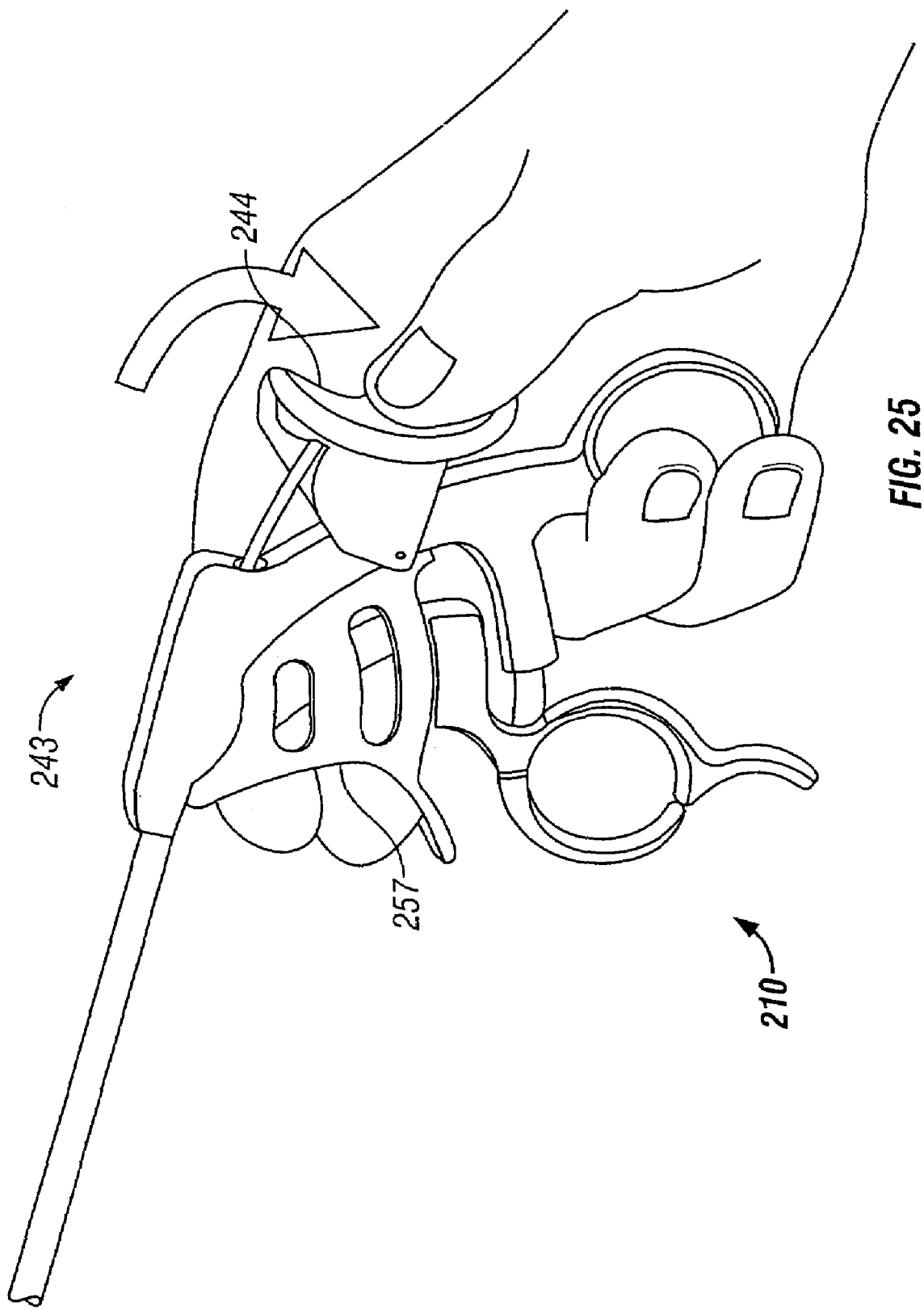
FIG. 25 is a perspective view of a handle assembly for the sixth preferred suturing apparatus including a preferred needle actuator.

In a rest state, as shown in original FIG. 23, the needle 224 is generally straight and may be biased to any rest position with respect to the ingress 228. For example, the rest position may comprise the notch 235 being disposed distally to the ingress 228, as shown in FIG. 23, or proximally to the ingress 228. To load a suture, the needle 224 is moved to a loading position whereby the notch 235 is aligned with the ingress 228 as shown in FIG. 24. If the needle 224 is biased such that the notch 235 is distal to the ingress 228, alignment is reached by moving the needle 224 in a proximal direction with respect to the first jaw 220. Accordingly, if the needle 224 were biased such that the notch 235 is proximal to the ingress 228, alignment is reached by moving the needle 224 in a distal direction with respect to the first jaw 220. FIG. 25 illustrates a preferred handle assembly 243 of the suturing apparatus 210. In FIG. 25, a manually operable actuator 244 is coupled to the needle to enable movement, both proximally and distally, thereof. In the illustrated embodiment, the actuator 244 preferably comprises a thumb lever, or rocker, that may be cocked backward by a user's thumb, thereby moving the needle proximally to align the notch with the ingress, and moved forward, thereby advancing the needle distally.

Figure 26:
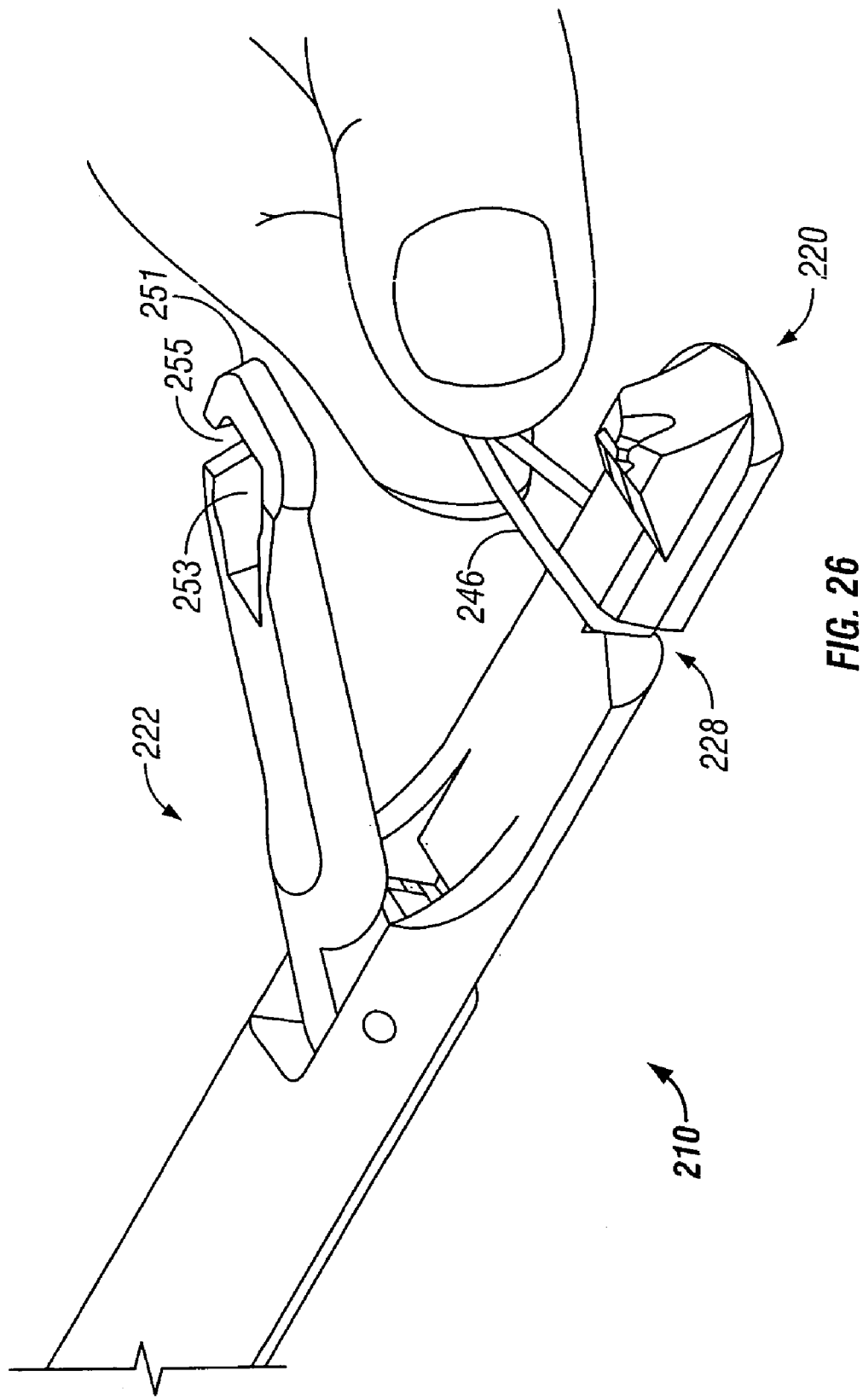
FIG. 26 is a perspective view of the sixth preferred suturing apparatus being loaded with a suture.
Figure 27:
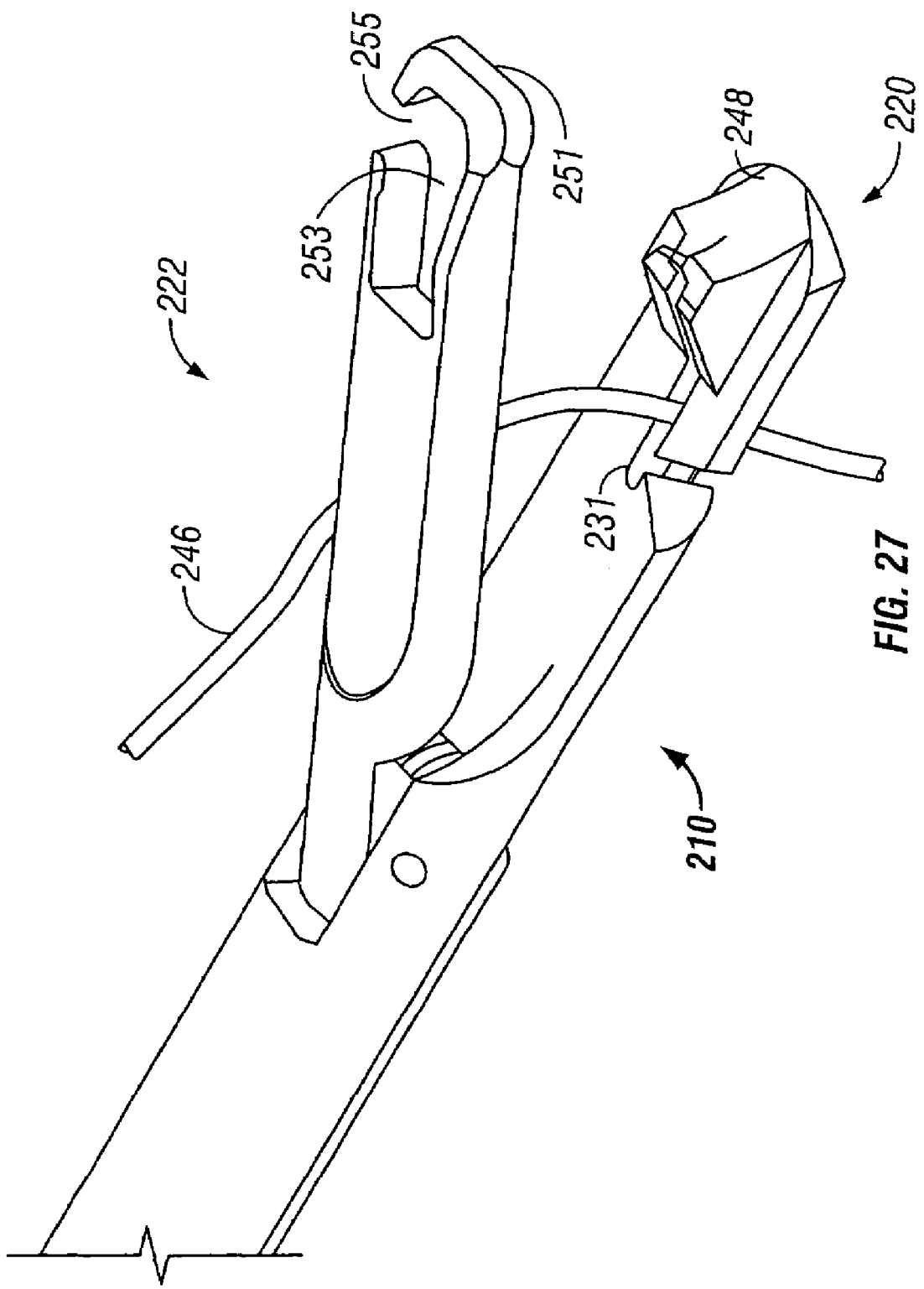
FIG. 27 is perspective view of the sixth preferred suturing apparatus with the suture loaded.

FIG. 26 illustrates a suture 246 being loaded onto the apparatus 210. The suture 246 is formed into a loop and threaded into the ingress 228. With the suture 246 held slightly taut across the first jaw 220, the suture 246 has entered the ingress 228 and is now disposed in the notch of the needle. The finger slide, shown in FIG. 25, may now be released, thereby distally biasing the needle with the captured suture 246 to the resting position as shown in FIG. 27. It will be appreciated that the axial slot 231 of the first jaw 220 allows the captured suture 246 to travel freely as it is carried by the needle 224.

A transition block 248 is provided at a distal portion of the first jaw 220 and may be integral with or separate from the jaw 220. The transition block 248 may be adapted to curve the needle and direct it at any desired angle, shown in the illustrated embodiment as generally perpendicular to the axis of the first jaw 220.

In FIGS. 26 and 27, the second jaw 222 comprises a distal hook 251 that defines an aperture 253 with a side opening 255. When the jaws 220, 222 are clamped on a piece of tissue, the aperture 253 is configured to enable the needle to pass through after piercing the tissue. As the needle 224 is retracted the tissue acts as suture receiver by holding on to the suture 246 while the needle 224 is withdrawn. This leaves a loop or free line of suture 246 on the side of the tissue in contact with the jaw 222. The hook 251 can then be placed in the loop and pulled. Alternatively, the two jaws 220, 222 can be grasped on the free line of suture and pulled through the tissue. In FIG. 25, a stationary finger support 257 serves as a counterforce plate for the actuator 244.

Figure 28:
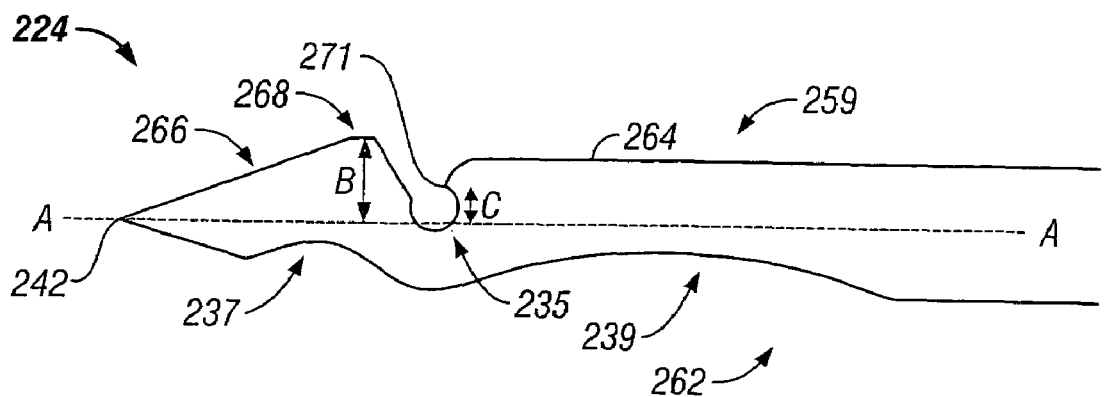
FIG. 28 is an elevation view of a preferred bendable needle according to the invention.

In FIG. 28, the preferred bendable needle 224 comprises a distal geometry that facilitates a smooth piercing of tissue by preventing the tissue from being snagged or caught by any part of the needle 224. The needle 224 comprises a notch side 259 and an opposite, void side 262. In particular, the needle 224 comprises a straight, notch-side edge 264 located proximally to a notch edge defining the notch 235. The needle 224 also defines a needle axis "A" that extends generally parallel to the notch-side edge 264.

As the needle 224 pierces a tissue, the tissue will travel along a notch-side ramp 266 that leads to a distal ledge 268 disposed distally of the notch edge defining the notch 235. As shown, a distal notch edge extends from the base and laterally from the axis for a first distance and a proximal notch edge that extends laterally from the base and laterally from the axis for a second distance that is less than the first distance. It will be appreciated that the distal ledge 268 is spaced a transverse distance "B" from the axis "A" while a proximal ledge 271 is spaced a transverse distance "C" from the axis "A." In the preferred embodiment, distance "B" is greater than distance "C" such that the distal ledge 268 pushes the pierced tissue outward to help keep the tissue from getting caught in the notch 235. As the tissue travels over the notch 235, a generally rounded bump that is associated with the proximal ledge 271 further prevents the tissue from getting snagged.

On the opposite, void side 262, first and second void edges define the first and second voids 237, 239 that distribute the stresses more evenly across the needle 224 and around the notch 235 when the needle 224 is bent, such that the stresses are minimized near the notch 235. The opening to the notch 235 is directed distally such that the suture is forced into the needle during deployment through the tissue and so that the suture releases easily as the needle is retracted.

Figure 29:
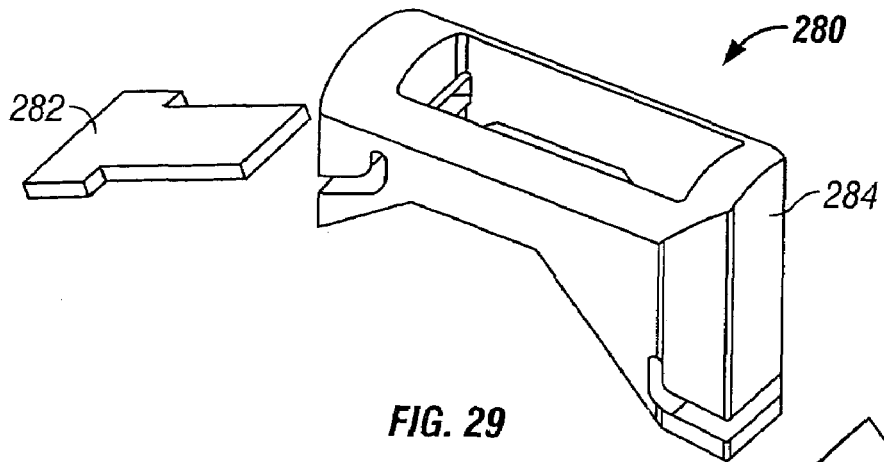
FIG. 29 is a partially exploded, perspective view of a preferred suture receiving mechanism.
Figure 30:
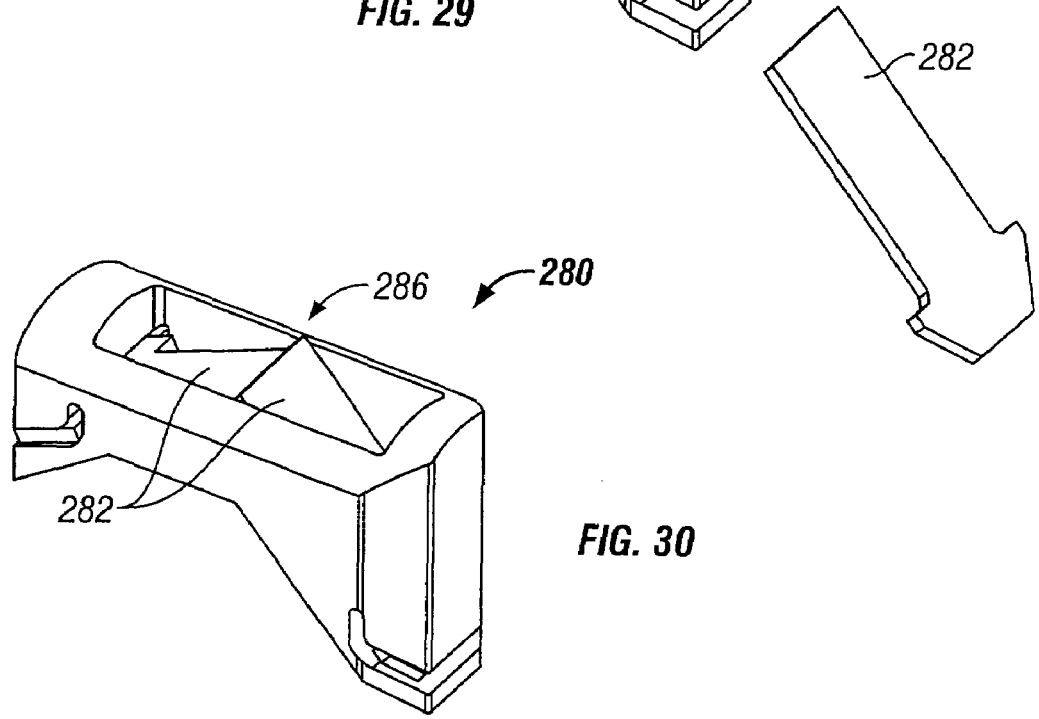
FIG. 30 is a perspective view of the preferred suture receiving mechanism of FIG. 29.

A further preferred embodiment of a suture receiver 280 is illustrated in FIGS. 29 and 30. The receiver 280 may, for example, be carried by a jaw opposite to the jaw housing a needle. The suture receiver 280 comprises a pair of flaps, or paddles, 282 disposed in a receiver housing 284. The paddles 282 are preferably configured to abut one another at a pinch point 286, as shown in FIG. 30, to permit a needle to travel therebetween while retaining a carried suture when the needle is retracted. As discussed above, employment of a suture receiver is optional as the pierced tissue itself may often times serve as a suture receiver. In particular, after a needle carrying a suture has pierced the piece of tissue, the pierced tissue often times sufficiently retains the suture in the form of a loop as the needle is retracted.

Figure 31:
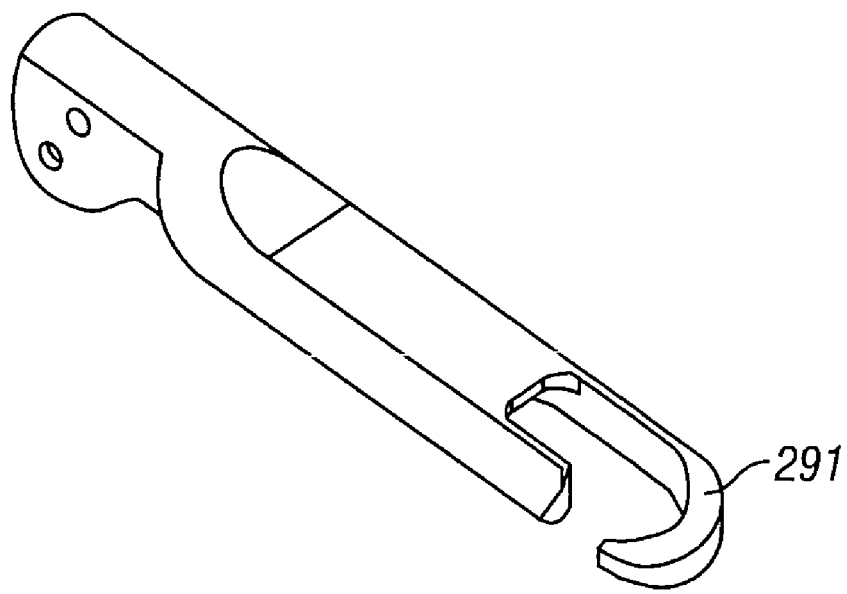
FIG. 31 is a perspective view of a jaw comprising a single barb.
Figure 32:
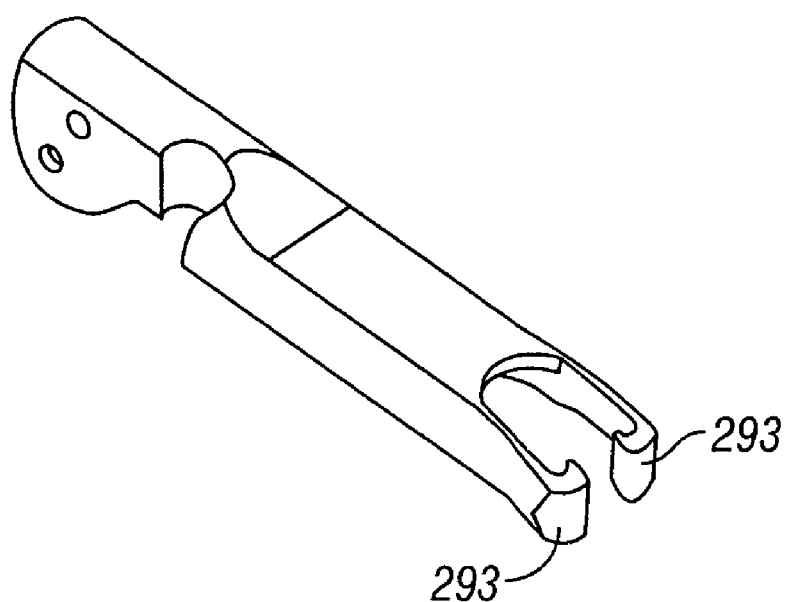
FIG. 32 is a perspective view of a jaw comprising a pair of barbs.

In FIG. 31, a first preferred embodiment of a hook, or barb 291, is formed at the distal end of a jaw, preferably the second jaw opposite to the first jaw housing the bendable needle. The barb 291 is configured to hook a looped suture that is retained, for example, by the tissue itself after the bendable has been retracted. In FIG. 32, a distal end of a jaw may alternatively be formed with a pair of barbs 293.

In all embodiments, it is to be expressly understood that a disposable needle may be employed. It will be appreciated, therefore, that a system or kit is provided wherein the suturing apparatus (excluding the needle) may be re-used while the disposable needles are replaced.

Many alterations and modifications may be made by those having ordinary skill in the departing from the spirit and scope of the invention. Therefore, it must be understood that the illustrated embodiments have been set forth only for the purposes of examples and that they should not be taken as limiting the invention as defined by the following claims. For example, notwithstanding the fact that the elements of a claim are set forth below in a certain combination, it must be expressly understood that the invention includes other combinations of fewer, more or different ones of the disclosed elements.

The words used in this specification to describe the invention and its various embodiments are to be understood not only in the sense of their commonly defined meanings, but to include by special definition in this specification the generic structure, material or acts of which they represent a single species.

The definitions of the words or elements of the following claims are, therefore, defined in this specification to not only include the combination of elements which are literally set forth. In this sense it is therefore contemplated that an equivalent substitution of two or more elements may be made for any one of the elements in the claims below or that a single element may be substituted for two or more elements in a claim. Although elements may be described above as acting in certain combinations and even initially claimed as such, it is to be expressly understood that one or more elements from a claimed combination can in some cases be excised from the combination and that the claimed combination may be directed to a subcombination or variation of a subcombination.

Insubstantial changes from the claimed subject matter as viewed by a person with ordinary skill in the art, now known or later devised, are expressly contemplate as being equivalently within the scope of the claims. Therefore, obvious substitutions now or later known to one with ordinary skill in the art are defined to be within the scope of the defined elements.

The claims are thus to be understood to include what is specifically illustrated and described above, what is conceptionally equivalent, what can be obviously substituted and also what incorporates the essential idea of the invention.

What is claimed is:

1. A needle adapted for use in a surgical suture device, the needle having an elongate configuration with an axis extending between a proximal end and a distal end, the axis dividing the needle into a notch side and a void side, the needle comprising:
    a sharp distal tip;
    a notch-side edge extending proximally of the tip;
    a notch-side ramp included in the notch-side edge and disposed proximally of the distal tip;
    a notch-side ledge included in the notch-side edge and disposed proximally of the notch-side ramp;
    a notch edge included in the notch-side edge and disposed proximally of the notch-side ledge;
    a void-side edge extending proximally of the tip; and
    a first void edge included in the void-side edge and disposed generally laterally opposite the notch-side ledge of the notch-side edge, the first void edge defining a first void having the shape of a first crescent of a first radius;
    a second void edge included in the void-side edge and disposed proximally of the first void edge and defining a second void having the shape of a second crescent of a second radius greater than the first radius.

2. The needle recited in claim 1 wherein the notch edge includes:
    a distal notch edge extending laterally from the axis a first distance; and
    a proximal notch edge extending laterally from the axis a second distance less than the first distance.

3. The needle recited in claim 2, wherein:
    the distal notch edge extends outwardly with progressive distal positions along the axis.

4. A needle adapted for use in a surgical suture device, comprising:
    a body having a generally straight, narrow and elongate configuration when in a rest state, with an axis thereof extending between a proximal end and a distal end;
    a sharp needle tip at the distal end of the body, a distal portion of the body near the sharp needle tip being generally flat and having a first side and a second side on opposite sides of the axis; and
    a slot configured to carry a suture therein located on the first side and at or near the distal end of the body and proximal to the sharp needle tip, the slot including an opening that is directed distally to carry a suture distally forward through tissue when the needle is moved in a distal direction and to release the suture when the needle is moved in a proximal direction,
    the distal portion of the body formed from a bendable material that enables a distal portion, including the sharp needle tip and the slot, to bend on a curve to an angle relative to the axis when pushed against an operative portion of the surgical suture device, and subsequently return to the generally straight configuration, through the application of an axial force that is comparable in magnitude to that provided by a user's thumb, and further comprising:
    a distal ledge disposed distally of the opening of the slot on the first side of the needle body, the distal ledge located at a first distance from the axis;
    a proximal ledge disposed proximally of the opening of the slot on the first side of the needle body, the proximal ledge located at a second distance from the axis that is shorter than the first distance such that the distal ledge pushes tissue out beyond the proximal ledge to prevent the tissue from getting caught in the slot when the needle is moved distally through tissue with the suture in the slot; and a distal ramp leading from the sharp needle tip to the distal ledge.

5. The needle recited in claim 4, further comprising a void disposed on the second side.

6. The needle recited in claim 5, wherein the void is a first void positioned proximally of the sharp needle tip and distally of the slot, the needle further comprising a second void positioned proximally of the first void.

7. The needle recited in claim 6, wherein the first void has a first axial length and the second void has a second axial length greater than the first axial length.

8. The needle recited in claim 6, wherein:
the first void has a first general shape of a first crescent with a first radius; and
the second void has a second general shape of a second crescent with a second radius greater than the first radius.

* * * * *